United States Patent [19]

Koenig, Jr.

[11] Patent Number: 5,443,838
[45] Date of Patent: Aug. 22, 1995

[54] NUTRITIONAL SUPPLEMENTATION SYSTEM

[76] Inventor: Steven M. Koenig, Jr., 4520 Toby La., Metairie, La. 70003-7630

[21] Appl. No.: 121,749

[22] Filed: Sep. 15, 1993

[51] Int. Cl.⁶ .............................................. A61K 9/48
[52] U.S. Cl. ................................. 424/439; 424/451; 424/456
[58] Field of Search ........................ 424/439, 451, 456

[56] References Cited

U.S. PATENT DOCUMENTS

| | | | |
|---|---|---|---|
| 4,973,467 | 11/1990 | Sahley | 424/439 |
| 4,980,168 | 12/1990 | Sahley | 424/439 |
| 5,051,258 | 9/1991 | Sahley | 424/439 |
| 5,164,384 | 11/1992 | Paul | 514/188 |

*Primary Examiner*—Thurman K. Page
*Assistant Examiner*—James M. Spear
*Attorney, Agent, or Firm*—Joseph T. Regard, Ltd.

[57] ABSTRACT

A three (3) stage process of nutritional supplementation used on a daily basis with varying dosages & ingredients for the three stages, morning, pre-workout, and night stages, in combination with at least one work-out during the day. The third or night stage is the opposite of that for the second, pre-work-out stage, with the third or night stage using no stimulants and the latter heavy stimulants, with the second, pre-work-out stage using heavy stimulants. Exemplary, preferred ingredient, dosages and times of day for the three (3) stages are disclosed.

14 Claims, No Drawings

NUTRITIONAL SUPPLEMENTATION SYSTEM

TECHNICAL FIELD

The present invention is directed to a nutritional supplementation system used for the betterment of heath, in which one's basic nutritional diet is supplemented in three distinct stages—morning, pre-workout and night, using varying dosages and ingredients in the dietary supplements.

BACKGROUND ART

The prior art does not contain any individual "prior art" reference which disclosed all aspects of the invention, but only showed that some of the individual aspects of the invention were known, typically in non-analogous situations.

The below listed patents are believed to be exemplary of the prior art.

| | |
|---|---|
| 4,973,467 | 4,980,168 |
| 5,051,258 | 5,164,384 |

For example, the three patents to Sahley (U.S. Pat. No. 4,973,467, 4,980,168 & 5,051,258) owned by Natrol, Inc. of Chatsworth, Calif., are directed to specific dietary supplements for adults and children, respectively, which have as one of their basic ingredients "GABA" (gamma-aminobutyric acid). Each patent then includes other various ingredients to be used with GABA.

The patent to Paul (U.S. Pat. No. 5,164,384) owned by Metagenics, Inc. of San Clemente, Calif., is directed to an anabolic mineral formula for use as a nutritional supplement, which formula includes vanadyl sulfate as its major ingredient, along with other ingredients.

None of these noted patents suggests the three stage, varying supplement approach of the invention having the same or an analogous formulation as the invention.

The present invention provides a more effective dietary supplementation system for the betterment of health than that achieved in the prior art.

GENERAL DISCUSSION OF INVENTION

The present invention involves preferably a three (3) stage process of nutritional supplementation used on a daily basis with varying dosages & ingredients for the three stages—morning, pre-workout, and night stages—in combination with at least one work-out during the day. The third or night stage is the opposite of that for the second, pre-work-out stage, with the former using preferably no stimulants and the latter heavy stimulants.

A purpose of splitting the dietary supplementation into three parts of the day is because one needs the opposite at night than one needs before a workout. It is believed that no other such supplementation system includes the approach of breaking the supplements distinctly down to morning, pre-workout, and night stages.

Particular, exemplary ingredients or components for the nutritional supplements of the invention included in the three, different, distinct stages are described in detail below.

In general the morning the user takes light stimulants, before a workout the user takes heavy stimulants and at night the user takes no stimulants.

Preferably the ingredient vanadyl sulfate is taken throughout the day but the dosage of it is the heaviest before a workout. The GABA (gamma aminobutyric acid) is given throughout the day but heaviest at night, because it elevates ones natural growth hormone output and causes the user's muscles to grow while sleeping. Caffeine, which is a stimulant, is taken heavily before a workout and only lightly in the morning.

Ephedrine (Ephedra) is also a stimulant, whose dosage in the preferred, exemplary embodiment of the invention is very light in the morning and heavy before a workout. Ephedrine HCL is taken only before a workout and in a moderate dosage of, for example, fifty (50 mg) milligrams. A variation of this is that the Ephedrine HCL is sometimes taken at a heavy dosage of, for example, one hundred (100 mg) milligrams. It should be noted that there is a significant difference between Ephedra and Ephedrine HCL.

Also, an off week is sometimes added after using the preferred system of the invention for, for example, four weeks so that the body does not get "used to" the dietary supplements being used.

Another exemplary variation is to seriously increase the dose of caffeine before a workout to, for example, about five hundred (500 mg) milligrams, or even seven hundred and fifth (750 mg) milligrams, or even a thousand (1000 mg) milligrams. Caffeine definitely enhances the benefits of hard exercising which in turn in synergistic combination enhances muscular growth, while it does not have this beneficial effect when combined with light or less exercise.

For purposes of comparison, it is noted that two (2) cups of coffee have about two hundred (200 mg) milligrams of caffeine in it.

However, it is noted that a problem occurs if all of the ingredients noted above and below are put into a mixed powder form. Instead, it is preferable that the ingredients be put into, for example, gelcaps, for consumption, so that the ingredients are protected against stomach acids, the exposure to which would cause the ingredients to loose their potency, or at least have their potency significantly reduced.

It is thus a basic object of the present invention to provide a nutritional supplementation system, including the use of varying ingredients and dosages taken in different, distinct stages, preferably three (morning, pre-workout and night), for one's nutritional diet, which system is used for the betterment of health and which is more effective than those of the prior art.

MODES FOR CARRYING OUT THE INVENTION

The preferred, exemplary embodiment of the methodology of the present invention involves a three (3) stage process of nutritional supplementation used on a daily basis with varying dosages & ingredients for the three stages, morning, pre-workout, and night stages, in combination with at least one workout during the day. The third or night stage is the opposite of that for the second, pre-workout stage, with the former using no stimulants and the latter heavy stimulants.

In the morning the user takes light stimulants, before a workout the user takes heavy stimulants, and at night the user takes no stimulants.

The ingredient vanadyl sulfate is taken throughout the day but the dosage of it is the heaviest before a workout. The GABA (gamma aminobutyric acid) is given throughout the day but heaviest at night because, inter alia, it elevates ones natural growth hormone output and causes the user's muscles to grow while sleeping. Caffeine, which is a stimulant, is taken heavily before a workout but only lightly in the morning.

Ephedrine (Ephedra) is also a stimulant, whose dosage is very light in the morning and heavy before a workout. Ephedrine HCL is taken only before a workout and in a moderate dosage of, for example, fifty (50 mg) milligrams. A variation of this is that the Ephedrine HCL is sometimes taken at a heavy dosage of, for example, one hundred (100 mg) milligrams.

Also, preferably an off week is sometimes or intermittently added after using the dosages and ingredients for, for example and preferably, four weeks or thereabouts, so that the body does not "get used" to it.

Another variation is to seriously increase the dose of caffeine before a workout to, for example, about five hundred (500 mg) milligrams, or even seven hundred and fifth (750 mg) milligrams, or even a thousand (1000 mg) milligrams.

It is preferable that the ingredients be put into, for example, gelcaps when the supplements are manufactured or at least before the user consumes them.

Exemplary times of the day for the taking the dietary supplementations in the three stages of the exemplary embodiment are, for example:

STAGE 1—8:30–9:30 AM for the morning stage or preferably right after awakening;

STAGE 2—within, for example, about fifteen to thirty (15–30) minutes of the beginning of the daily workout, which workout preferably is done not earlier than late morning or early afternoon and typically is done in the evening hours; and STAGE 3—9:30–11:30 PM for the night stage preferably right before bedtime.

Particular examples for the supplement are presented below, along with exemplary, acceptable ranges for the ingredients.

| EXEMPLARY NUTRITIONAL SUPPLEMENTS | | | |
|---|---|---|---|
| | Example 1 | | |
| Morning | Ephedrine | 10 | mg |
| | Caffeine | 25 | mg |
| | Vanadyl Sulfate | 20 | mg |
| | GABA | 3 | grams |
| Preworkout Scoop | Ephedrine HCL | 50 | mg |
| | Caffeine | 125 | mg |
| | Ephedrine | 100 | mg |
| | Vanadyl Sulfate | 50 | mg |
| | GABA | 1 | gram |
| Night | GABA | 4 | grams |
| | Vanadyl Sulfate | 10 | mg |
| | Example 2 | | |
| Morning | Ephedrine | 10 | mg |
| | Caffeine | 25 | mg |
| | Vanadyl Sulfate | 20 | mg |
| | GABA | 3 | grams |
| Preworkout Scoop | Ephedrine HCL | 100 | mg |
| | Caffeine | 300 | mg |
| | Ephedrine | 100 | mg |
| | Vanadyl Sulfate | 80 | mg |
| | GABA | 1 | gram |
| Night | GABA | 5 | grams |
| | Vanadyl Sulfate | 10 | mg |
| Ranges of Ingredients | | | |
| Ingredient | Minimum | Maximum | |
| Epedrine HCL | 1 mg | 500 mg | |
| Caffeine | 1 mg | 1,500 mg | |
| Ephedra | 1 mg | 1,000 mg | |
| Vanadyl Sulfate | 1 mg | 1,000 mg | |
| GABA | 200 mg | 20 grams | |
| Ginseng | 1 mg | 1,500 mg | |

Ginseng is an example of an alternative ingredient that could be added. It preferably would be added to the pre-workout scoop in order to add an extra, antifatigue effect. An exemplary, proper dose would be about two hundred and fifty (250 mg) milligrams.

It is further noted that an exemplary "workout" in the context of this invention typically comprises going to a health spa or gym or using like home exercise equipment for intense exercise, primarily weight-lifting, for approximately an average of about ninety (90) minutes. In such a workout the user is primarily interested in muscular development. Additionally, it should be understood that the nutritional supplementation of the invention is an integral part of such a muscular growth regime and is totally different from and non-analogous to multi-stage diet systems which do not involve significant weight lifting and are typically followed by the elderly, sick and infirm.

Of course the invention is subject to many variations in detail, dosages and methodology and the foregoing disclosure should be considered merely exemplary except where otherwise indicated.

Because many varying and different embodiments may be made within the scope of the inventive concept(s) herein taught, and because many modifications may be made in the embodiments herein detailed in accordance with the descriptive requirements of the law, it is to be understood that the details herein are to be interpreted as illustrative and not in a limiting sense.

I claim:

1. A method of supplementing one's nutritional diet, comprising the following steps:
 a) performing on a substantially daily basis three stages of nutritional supplementation, morning, pre-workout, and night stages, by ingesting different, varying dosages and nutritional ingredients in three stages, the third or night stage using no stimulants and the pre-work-out stage utilizing heavy stimulants, comprising the substeps of
 i. in the morning stage, ingesting in combination, a stimulant, vanadyl sulfate, and GABA;
 ii. in the pre-workout stage, ingesting in combination, a greater dosage of stimulant than in the morning stage, vanadyl sulfate, and GABA; and
 ii. In the night stage, ingesting in combination, GABA and vanadyl sulfate, with no stimulants;
 b) performing at least one work-out on a substantially daily basis after said second stage;
thereby enhancing one's health and nutritional well-being.

2. The method of claim 1, wherein said three stages are performing within the following time ranges:
 about 8:30–9:30 AM for the morning stage;
 within about thirty (30) minutes of the beginning of the daily workout, which workout is done no earlier than late morning; and
 9:30–11:30 PM for the night stage.

3. The method of claim 1, wherein there is further included the step of:
 taking vanadyl sulfate throughout the three stages of the day, with the heaviest dosage of it in the pre-workout stage.

4. The method of claim 1, wherein there is further included the step of:
 taking GABA (gamma aminobutyric acid) throughout the day, with the heaviest dosage of it in the night stage, elevating the user's natural growth hormone output and causing the user's muscles to grow while sleeping.

5. The method of claim 1, wherein there is further included the step of:
taking a light dosage of Ephedrine (Ephedra) in the morning stage and a heavy dosage in the pre-workout stage.

6. The method of claim 1, wherein there is further included the step of:
taking Ephedrine HCL only in the pre-workout stage.

7. The method of claim 6, wherein there is further included the step of:
taking Ephedrine HCL and in a moderate dosage of about fifty (50 mg) milligrams.

8. The method of claim 6, wherein there is further included the step of:
taking Ephedrine HCL in a heavy dosage of about one hundred (100 mg) milligrams.

9. The method of claim 1, wherein there is further included the step of:
taking a heavy dosage of caffeine in the pre-workout stage but in only a light dosage in the morning stage.

10. The method of claim 9, wherein there is further included the step of:
taking the dose of caffeine in the pre-workout stage in a dosage of at least about five hundred (500 mg) milligrams.

11. The method of claim 1, wherein there is further included the step of:
adding an off-week after using the dosages and ingredients for about four weeks.

12. The method of claim 1, wherein there is further included the step of:
putting the ingredients into gelcaps in each stage before the user consumes them.

13. The method of claim 1, wherein the ingredients and dosage for each stage are about as follows:

| Morning Stage | Ephedrine | 10 mg |
|---|---|---|
| | Caffeine | 25 mg |
| | Vanadyl Sulfate | 20 mg |
| | GABA | 3 grams |
| Preworkout Stage | Ephedrine HCL | 50 mg |
| | Caffeine | 125 mg |
| | Ephedrine | 100 mg |
| | Vanadyl Sulfate | 50 mg |
| | GABA | 1 gram |
| Night Stage | GABA | 4 grams |
| | Vanadyl Sulfate | 10 mg. |

14. The method of claim 1, wherein the ingredients and dosage for each stage are about as follows:

| Morning Stage | Ephedrine | 10 mg |
|---|---|---|
| | Caffeine | 25 mg |
| | Vanadyl Sulfate | 20 mg |
| | GABA | 3 grams |
| Preworkout Stage | Ephedrine HCL | 100 mg |
| | Caffeine | 300 mg |
| | Ephedrine | 100 mg |
| | Vanadyl Sulfate | 80 mg |
| | GABA | 1 gram |
| Night Stage | GABA | 5 grams |
| | Vanadyl Sulfate | 10 mg. |

* * * * *